United States Patent
Lee et al.

(10) Patent No.: US 6,758,227 B2
(45) Date of Patent: Jul. 6, 2004

(54) MEDICAL INSTRUMENT WASHER

(75) Inventors: Tae Hee Lee, Seoul (KR); Dae Yeong Han, Seoul (KR); Jin Woong Kim, Kyonggi-do (KR); Si Moon Jeon, Seoul (KR)

(73) Assignee: LG Electronics Inc., Seoul (KR)

( * ) Notice: Subject to any disclaimer, the term of this patent is extended or adjusted under 35 U.S.C. 154(b) by 175 days.

(21) Appl. No.: 10/042,150

(22) Filed: Jan. 11, 2002

(65) Prior Publication Data
US 2002/0185165 A1 Dec. 12, 2002

(30) Foreign Application Priority Data
Jun. 9, 2001 (KR) .................................. 2001-0032304

(51) Int. Cl.⁷ ................................................ B08B 3/02
(52) U.S. Cl. ............... 134/99.1; 134/103.3; 134/168 C; 134/170; 422/300
(58) Field of Search .................. 134/56 D, 57 D, 134/94.1, 95.3, 99.1, 103.3, 166 R, 167 R, 168 C, 169 C, 167 C, 170, 171, 176, 179, 198; 422/297, 300

(56) References Cited
U.S. PATENT DOCUMENTS

| | | | |
|---|---|---|---|
| 1,581,528 A | * | 4/1926 | Andersson |
| 2,786,480 A | * | 3/1957 | Hofer |
| 3,070,104 A | * | 12/1962 | Faust et al. |
| 3,616,806 A | * | 11/1971 | Randall |
| 4,179,307 A | * | 12/1979 | Cau et al. ............... 134/58 D |
| 5,010,660 A | * | 4/1991 | Hambleton et al. |
| 5,279,799 A | * | 1/1994 | Moser |
| 5,380,369 A | * | 1/1995 | Steinhauser et al. |
| 5,533,539 A | * | 7/1996 | Sutter et al. |
| 5,554,228 A | * | 9/1996 | Giordano et al. |
| 5,738,824 A | * | 4/1998 | Pfeifer |
| 5,749,385 A | * | 5/1998 | Rochette et al. |

FOREIGN PATENT DOCUMENTS

JP 9-38592 * 2/1997

* cited by examiner

Primary Examiner—Frankie L. Stinson
(74) Attorney, Agent, or Firm—Fleshner & Kim, LLP

(57) ABSTRACT

A medical instrument washer is provided which includes a rack drawably fitted in a washing tub, for setting washing objects thereon, a flow passage having one end located on a rear side of the washing tub for supplying washing water to the rear side, and a washing duct on the rack having a washing water inlet in rear part thereof so as to be detachably connected to one end of the flow passage as the rack is drawn/pushed in. The medical instrument washer so constructed reduces washing water quantity, and pressure loss of washing water by improving a flow passage of the medical instrument washer.

10 Claims, 4 Drawing Sheets

MEDICAL INSTRUMENT WASHER

BACKGROUND OF THE INVENTION

1. Field of the Invention

The present invention relates to a medical instrument washer, and more particularly, to a flow passage of a medical instrument washer.

2. Background of the Related Art

Referring to FIG. 1, a related art medical instrument washer is, in general, provided with a body 1 divided into a washing tub 2, and a pump room 3, an upper rack 4, and a lower rack 5 drawably fitted in the washing tub 2, an upper spray arm 4a in a lower part of the upper rack 5 for spraying washing water toward the upper rack 4 an extension tube 4b vertically disposed in an upper part of the upper rack 4 having one end connected to the upper spray arm 4a for supplying washing water to the upper spray arm 4a, and a lower spray arm 5a in a lower part of the lower rack 5 for spraying washing water toward the lower rack 5. The related art medical instrument washer is also provided with a sump 6 in the pump room 3 for collecting washing water supplied to the washing tub 2, or returned after washing, a washing pump 7 connected to the sump 6 for discharging washing water in the sump 6 to the upper/lower spray arms 4a, and 5a, a first flow passage 8 having one end connected to the washing pump 7, the other end connected to the other end of the extension tube 4b, and a body part arranged along a rear surface of the washing tub 2 for supplying washing water to the upper spray arm 4a, and a second flow passage 9 having one end connected to the washing pump 7, the other end connected to the lower spray arm 5a for supplying washing water to the lower spray arm 5a.

The operation of the foregoing medical instrument washer will be explained.

Upon pushing in the upper and/or lower rack 4/5 into the washing tub 2 after the user sets washing objects (medical instruments) on the upper and/or lower rack 4/5, the other end of the extension tube 4b is engaged with the other end of the first flow passage 8. Then, a door 1a in front part of the body us closed, and a starting button is pressed, to put the medical instrument washer into operation. Then, as water is supplied, and the washing pump 7 comes into operation, the supplied washing water is drawn into the washing pump 7 through the sump 6. By pumping of the washing pump 7, the washing water is pressed to the upper spray arm 4a and the lower spray arm 5a along the first flow passage 8 and the second flow passage 9 respectively, and sprayed through spray nozzles in the spray arms 4a and 5a toward the upper/lower racks 4, and 5 respectively, thereby washing the medical instruments.

However, the first flow passage 8 of the related art medical instrument washer is too long with additional extension tube 4b, to cause an excessive pressure loss of the washing water as a quantity of the washing water increases. That is, since one end of the first flow passage 8 starts from the washing pump 7, is lead to the upper part of the washing tub 2 along the rear surface of the washing tub 2, and the other end of the first flow passage 8 is connected to the extension tube 4b located in the upper rack 4 part, loss of washing water quantity and pressure drop caused by the lengthy first flow passage 8 have been problems.

SUMMARY OF THE INVENTION

Accordingly, the present invention is directed to a medical instrument washer that substantially obviates one or more of the problems due to limitations and disadvantages of the related art.

An object of the present invention is to provide a medical instrument washer, in which a flow passage is improved for reducing loss of washing water quantity, and pressure loss to the maximum.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, the medical instrument washer includes a rack drawably fitted in a washing tub, for setting washing objects thereon, a flow passage having one end located on a rear side of the washing tub for supplying washing water to the rear side, and a washing duct on the rack having a washing water inlet in rear part thereof so as to be detachably connected to one end of the flow passage as the rack is drawn/pushed in.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENT

Reference will now be made in detail to the preferred embodiments of the present invention, examples of which are illustrated in the accompanying drawings. Parts of the present invention identical to the related art will be given the same reference symbols.

Figure 1:
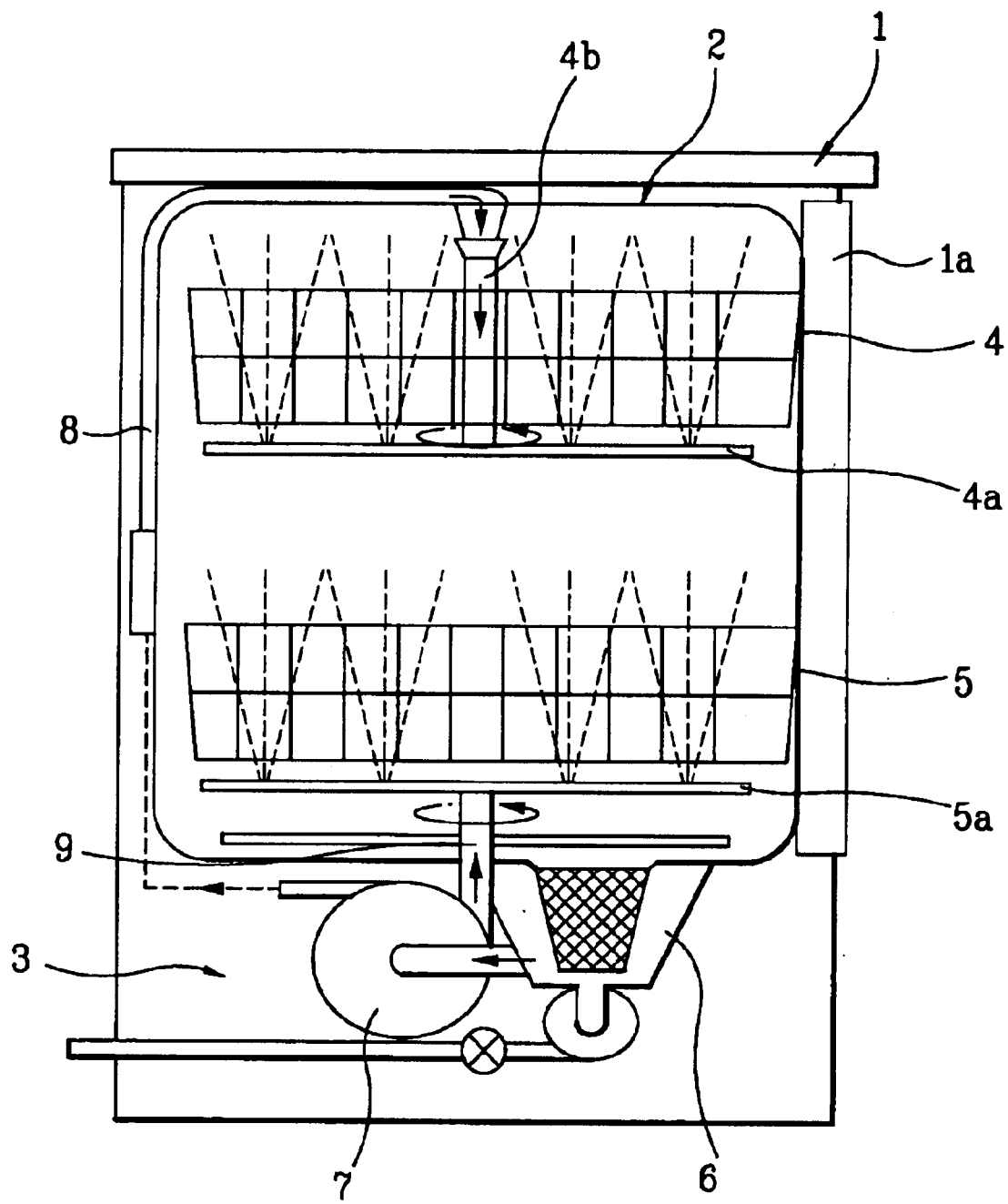
FIG. 1 illustrates a section of a related art medical instrument washer.
Figure 2:
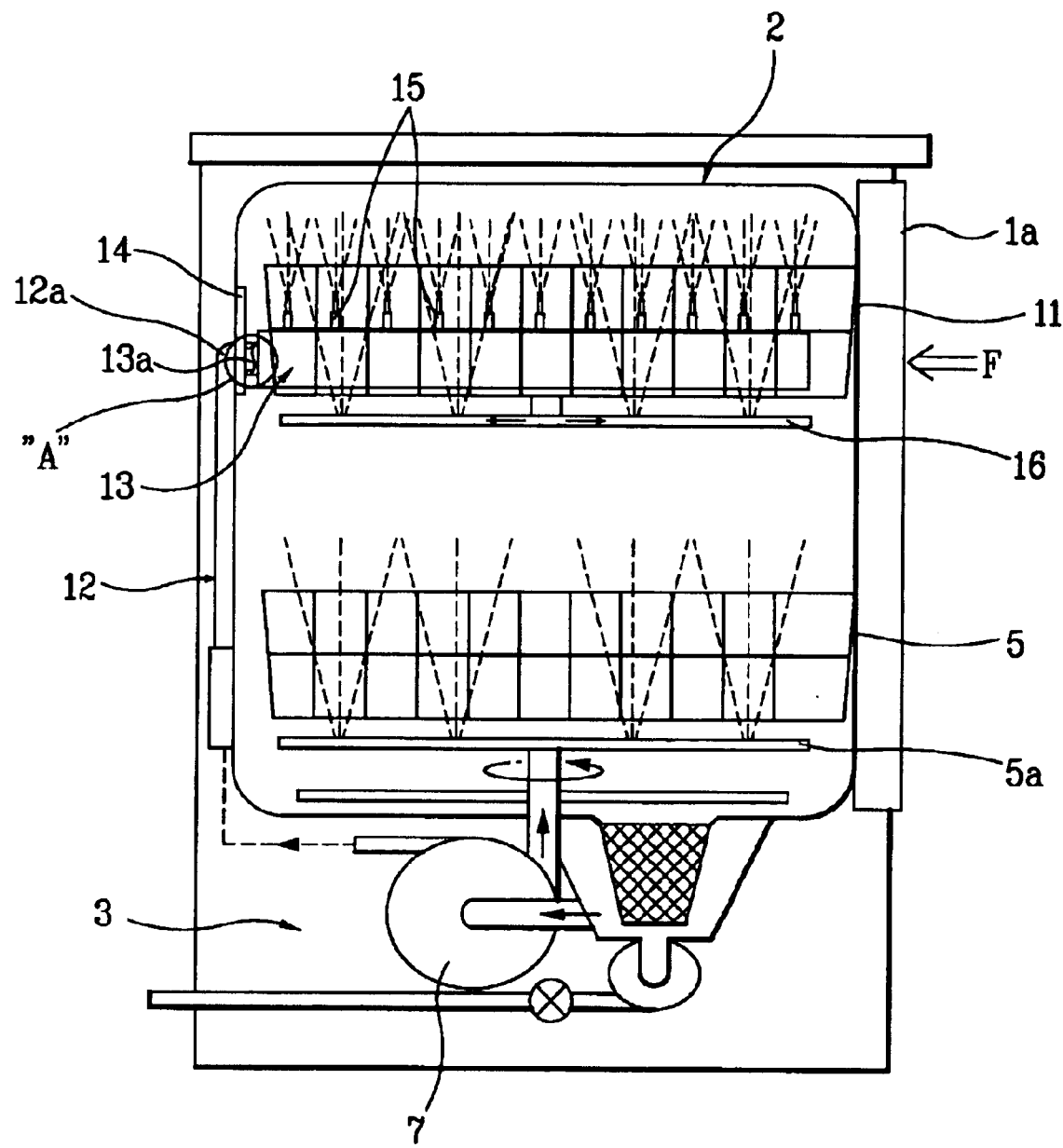
FIG. 2 illustrates a section of a medical instrument washer in accordance with a preferred embodiment of the present invention.
Figure 3:
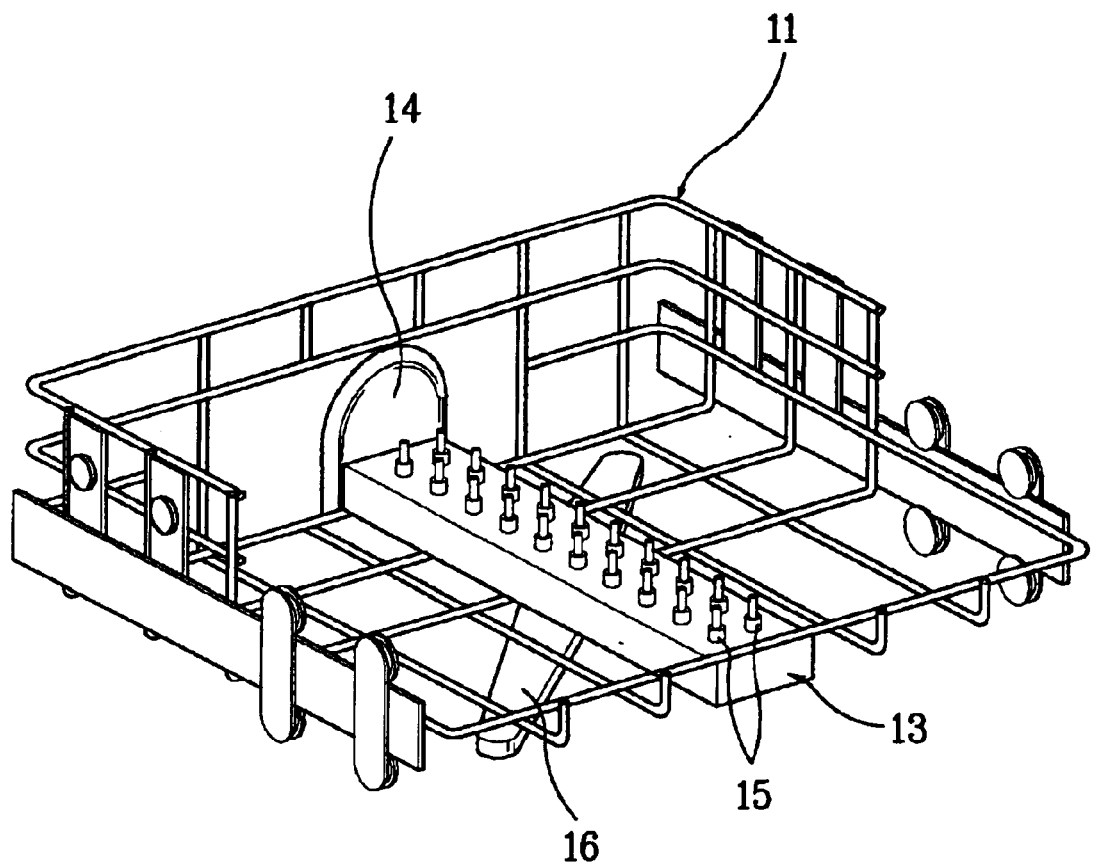
FIG. 3 illustrates a perspective view of a washing duct and rack of the present invention.

Referring to FIGS. 2, or 3, the medical instrument washer in accordance with a preferred embodiment of the present invention includes an upper rack 11 drawably fitted in a washing tub 2, for setting washing objects, a flow passage 12 having one end 12a located on a rear side of the washing tub for supplying washing water to the rear side, and a washing duct 13 on the upper rack having a washing water inlet 13a in rear part thereof so as to be detachably connected to one end 12a of the flow passage as the upper rack 11 is drawn/pushed in.

It is preferable that an opening is provided in a front part of the washing tub 2 for draw/push in the upper rack 11, with a door in the opening so that the washing water inlet 13a in the washing duct 13 is pressed onto the one end 12a of the flow passage to make the washing water inlet 13a engaged with the one end 12a by a thrust generated when the upper rack 11 moves backward when the door is closed. Along with this, it is further preferable that there is a rubber member 14 around the washing water inlet 13a for a better sealing of the washing water inlet 13a with the one end 12a of the flow passage when the washing water inlet is connected to the one end 12a of the flow passage. The washing duct 13 may further be provided with an injector nozzle 15 on an upper surface thereof for exclusive washing of endoscopes. The washing duct 13 may have an upper spray arm 16 further connected to a bottom of the washing duct 13 for spraying washing water toward the upper rack 11. It is preferable that the flow passage 12 has one end 12a located at a rear side of the washing tub 2, and the other end connected to a washing pump 7 fitted below the washing tub 2.

The process for connecting the flow passage to the washing duct will be explained in detail, with reference to FIGS. 4A, and 4B.

Figure 4A:
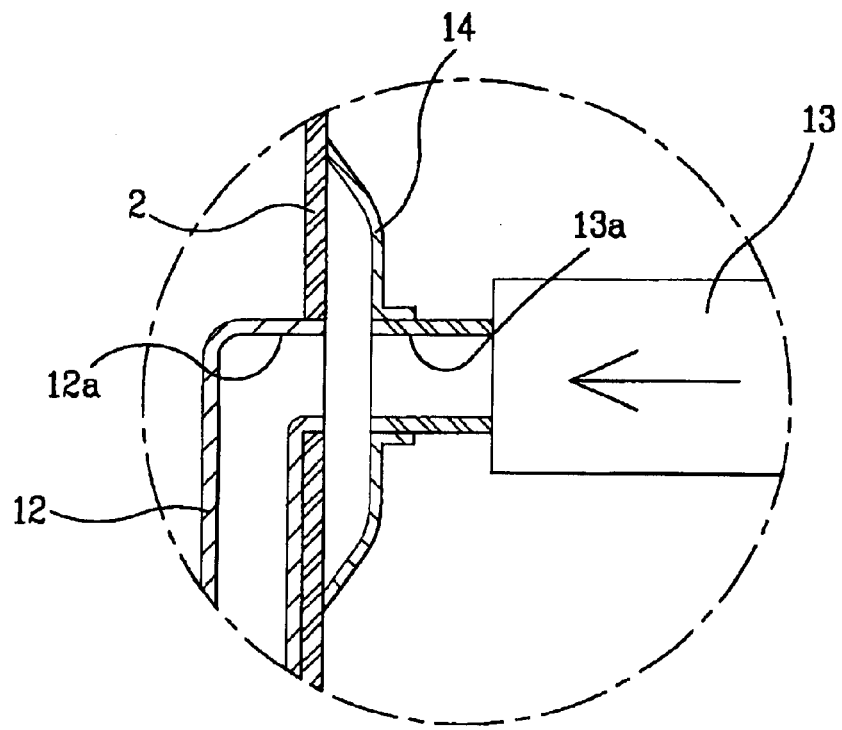
FIG. 4A illustrates a detail of "A" part in FIG. 2 showing a progress of operation of key parts of the present invention; and, FIG. 4b illustrates a detail of "A" part in FIG. 2 showing a completion of operation of key parts of the present invention.
Figure 4B:
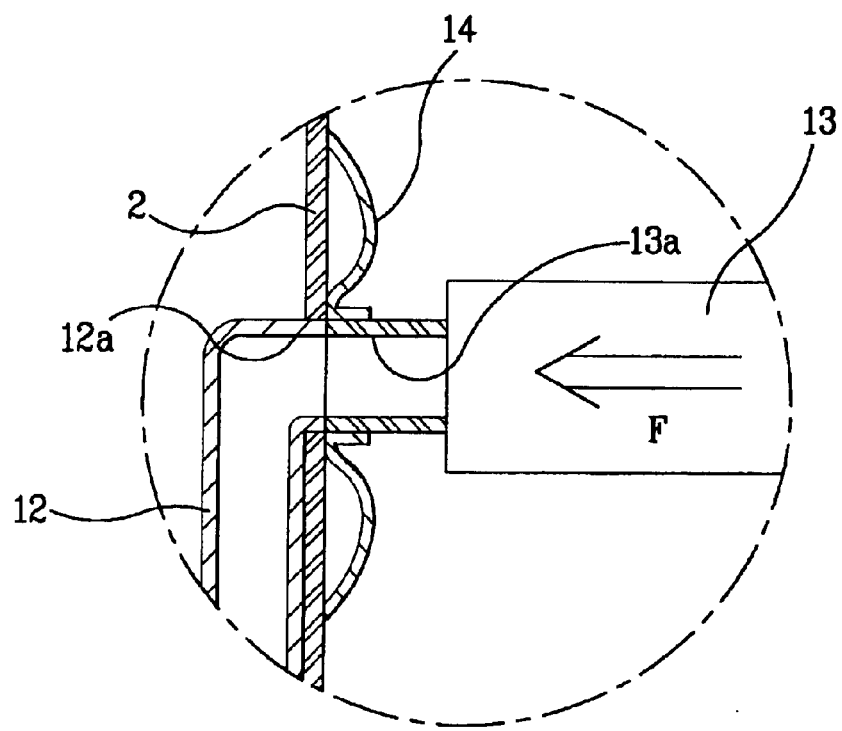

Referring to FIG. 4A, when the user pushes in the upper rack inside of the washing tub 2 after the user sets washing objects (medical instruments) on the upper rack 11, the rubber member 14 around the washing water inlet 13a of the washing duct 13 comes into contact with the one end 12a of the flow passage 12. Then, referring to FIG. 4B, upon closing the door 1a, the upper rack 11 is pushed back by a thrust of the door, such that the rubber member 14 around the washing water inlet 13a is pressed onto the one end 12a of the flow passage 12, to seal the one end 12a, thereby connecting the washing water inlet 13a to the one end 12a of the flow passage.

Referring to FIG. 2, when the door 1a is closed fully, the upper rack 11 is brought into contact with an inside wall of the door 1a to come into a standstill state, sustaining a continuous pressed sealing state of the washing water inlet 13a and the one end 12a of the flow passage 12. As the process hereafter is similar to the related art, further explanation of the process will be omitted.

It will be apparent to those skilled in the art that various modifications and variations can be made in the medical instrument washer of the present invention without departing from the spirit or scope of the invention. Thus, it is intended that the present invention cover the modifications and variations of this invention provided they come within the scope of the appended claims and their equivalents.

As has been explained, the medical instrument washer of the present invention has the following advantages.

The shortened flow passage permits to reduce loss of washing water quantity and washing water pressure drop to the maximum.

All advantages described in the detailed description of the preferred embodiment of the present invention are inclusive.

What is claimed is:

1. A medical instrument washer, comprising:
   a rack configured to be drawably fitted in a washing tub, and to receive washing objects thereon;
   a flow passage, wherein an end of the flow passage located on a rear side of the washing tub is configured to supply washing water to the tear side of the washing tub; and
   a washing duct positioned on the rack and having a washing water inlet in a rear portion thereof configured to be detachably connected to one end of the flow passage as the rack is drawn out or pushed in, wherein the washing duct comprises:
      a plurality of injector nozzles provided on a center portion of an upper surface of the washing duct, wherein the injector nozzles are configured to wash endoscopes placed on a center portion of the rack; and
      an upper spray arm provided on a lower surface of the washing duct and configured to spray washing water toward the rack so as to wash other medical instruments placed on side portions of the rack;
   and wherein the washing tub comprises:
      an opening provided in a front portion thereof; and
      a door provided in the opening such that, when the door is closed, the washing water inlet is engaged with the one end of the flow passage due to the backward motion of the door.

2. The medical instrument washer of claim 1, further comprising a rubber member provided on an outer portion of the washing water inlet configured to seal a connection between the washing water inlet and the one end of the flow passage.

3. The medical instrument washer of claim 1, wherein one end of the flow passage is located at a rear side of the washing tub, and the other end of the flow passage is connected to a washing pump fitted below the washing tub.

4. A washer, comprising:
   a rack configured to be drawn into and out of a washing container, and to receive a plurality of types of objects to be washed thereon;
   a flow passage configured to supply a fluid from an external source to a rear portion of the washing container; and
   a duct positioned on the rack and configured to be detachably connected at a rear portion thereof to one end of the flow passage as the rack is drawn into and out of the washing container, wherein the duct comprises:
      a plurality of injector nozzles provided on a center portion of an upper surface of the duct and configured to wash at least one of a first type of device placed on a center portion of the rack; and
      a spray arm provided on a lower surface of the duct and configured wash a plurality of other types of devices placed on side portions of the rack.

5. The washer of claim 4, wherein the washing container comprises:
   an opening provided in a front portion thereof and configured to draw out and push in the rack; and
   a door provided in the opening, such that, when the door is closed, an inlet of the duct is engaged with an end of the flow passage due to the backward motion of the door.

6. The washer of claim 5, further comprising a resilient member provided on an outer portion of the inlet and configured to seal a connection between the inlet of the duct and the end of the flow passage.

7. The washer of claim 4, wherein a first end of the flow passage is located at a rear side of the washing container, and a second end of the flow passage is connected to a washing pump provided below the washing container.

8. The washer of claim 4, wherein the first type of device comprises an endoscope.

9. The washer of claim 4, wherein the washer is configured to wash medical instruments.

10. The washer of claim 4, wherein the fluid comprises a cleaning fluid.

* * * * *